United States Patent [19]
Stephen et al.

[11] Patent Number: 5,301,688
[45] Date of Patent: Apr. 12, 1994

[54] METHOD FOR LOCALISATION AND THERAPY OF OCCULT BLADDER CANCER

[75] Inventors: Robert L. Stephen, Salt Lake City, Utah; Franco Lugnani, Trieste; Cino Rossi, Rome, both of Italy; Silvio Eruzzi, Mantova, Italy

[73] Assignee: Physion S.r.l., Mirandola, Italy

[21] Appl. No.: 925,780

[22] Filed: Aug. 7, 1992

[51] Int. Cl.⁵ ............................................. A61N 1/00
[52] U.S. Cl. ..................................... 607/99; 128/898; 604/20
[58] Field of Search ................... 128/784–786, 128/654, 804, 898, 7, 665; 604/20

[56] References Cited

U.S. PATENT DOCUMENTS

| | | | |
|---|---|---|---|
| 4,248,214 | 2/1981 | Hannah et al. | 604/20 |
| 5,002,956 | 3/1991 | Thiel | 514/297 |
| 5,066,274 | 11/1991 | Bommer et al. | 424/2 |
| 5,171,749 | 12/1992 | Levy et al. | 514/410 |

Primary Examiner—William E. Kamm
Assistant Examiner—Samuel Gilbert
Attorney, Agent, or Firm—Jacobson and Johnson

[57] ABSTRACT

Intravesical electromotive administration of specified dye substances for localisation and treatment of occult bladder cancers, is disclosed. Innocuous dye substances will provide differential staining of cancerous and normal urothelium; and anticancer dye substances will demonstrate differential staining and also initiate therapy of cancerous lesions. The addition of vasodilating agents will accentuate the differential staining and further promote therapy of the cancerous sites.

18 Claims, 2 Drawing Sheets

METHOD FOR LOCALISATION AND THERAPY OF OCCULT BLADDER CANCER

BACKGROUND OF THE INVENTION

1. Field of the Invention

The present invention relates to the diagnosis of cancer. In particular, this invention describes electromotive administration of dye substances into the bladder wall, with and without vasodilatation, for the localisation, or localisation and treatment, of occult cancerous sites in persons with diagnosed cancer of the bladder.

2. Description of Prior Art

Bladder Cancer

Origins: Cancer of the bladder is usually multifocal in nature with malignant changes in normal tissues appearing in multiple sites. This situation has given rise to two schools of thought: 1) bladder cancer is multiclonal in origin or; 2) it is monoclonal in nature with facilitated spread laterally through bladder tissues and/or dispersion of viable cancer cells throughout the bladder cavity to seed at other sites. The -merits of these two hypotheses are still unresolved but, whichever is correct, the important aspect related to this invention is the frequent occurrence of multiple tumors at different sites within the bladder wall.

Treatment of Bladder Cancer: Following diagnosis of bladder cancer, there are three mainstays of therapy.

1. Transurethral Resection (TUR) where an endoscope is inserted into the bladder, sites of cancerous tissue are located visually and then resected and cauterised using an electrically heated wire loop. Patients return to operating rooms on a regular schedule and any subsequent cancers are also treated by TUR, a repetitive series of events that often goes on for years. The most appealing aspect of this particular therapy is that there is very little morbidity: patients are performing their usual activities the next day and the resected areas of bladder tissue are fully healed in 7-10 days.
2. Radiotherapy is often employed when tumor penetration is too deep for successful TUR and there are debilitating long term side effects caused by generalised inflammation of the pelvic region.
3. Operative procedures include the rare partial cystectomy and the more common total cystectomy (bladder removal). This latter procedure constitutes major debilitating surgery and also mandates some form of urinary diversion.

In addition to the above treatments, anticancer drugs are sometimes used either systemically, or by local instillation into the bladder. Administered systemically these drugs have dangerous side effects, sometimes causing death, and when administered locally into the bladder, many expected benefits do not materialize because of the physiological functions of the bladder itself.

Pathology of Bladder Cancer: The great majority of bladder cancers are described as transitional cell carcinomas arising from the normal transitional cell epithelium (urothelium) lining the interior of the bladder wall. The degree of penetration (spread) of these tumors is graded conventionally, Ta $T_1$ $T_2$ $T_3$ $T_4$, with Ta being the most superficial and $T_4$ extending through and beyond the bladder wall into outlying tissues, as shown in FIG. 1. This Figure is a view of a longitudinal section of the bladder with the surrounding tissues. In particular the inner tissue is the urothelium (2), the second is the lamina propria (3) the third is the muscularis tissue (4) and the outermost is the perivescical tissue (5).

Malignant classification is also conventional, with $G_1$ being the most benign and $G_3$, $G_4$ the most anaplastic and rapidly spreading. Hicks et al. (The ultrastructure and chemistry of the luminal plasma membrane of the mammalian urinary bladder: a structure with low permeability to water and ions. Philos Trans R Soc Lond (Biol). 1974; 268:23-38); demonstrated that cancer cells, both singly and in groups, display greater permeability to water and solutes than do the normal cells from which they arise; and the more anaplastic the cancer, the greater the permeability.

When viewed through an endoscope, many cancers may appear as papillomatous growths extending into the bladder cavity, as ulcers eroding the bladder wall or as combinations of the two. On direct viewing with an endoscope, flat (endophytic) cancers are often missed and carcinoma in situ (CIS) (6) which consists of discrete clumps of cancer cells buried in normal tissue, is almost always missed.

Blood Supply: Pertinent to this invention is the blood supply to cancerous tissue. As tumors grow they simply push normal blood vessels to one side and generate their own blood vessels by a process termed "angiogenesis". These new blood vessels are distinctly abnormal and form an interlacing network that becomes more abnormal the more anaplastic the cancers, and they take on the appearance of a series of interconnected lagoons in the highly malignant $G_3$ and $G_4$ tumor types. All of these abnormal blood vessels are of more or less fixed diameter, so that blood flow rate ($Q_B$) through these same vessels responds to pressure changes only and is not responsive to the variety of physical (hot and cold) and chemical (drugs) agents that dilate and constrict normal blood vessels. Thus it is possible to vary, in a controlled manner, the differential in blood flow ($\Delta Q_B$) between cancerous tissue and surrounding normal tissues by selective application for one or more vasoactive physical or chemical agents.

Localisation of Bladder Cancer with Dyes

As long as visual detection remains the method of chaise for localisation of abnormal (Pre malignant or malignant) urothelium, the best way of improving detection rates is by selective staining of abnormal sites so that the viewer may select these regions by their color differences from normal surrounding tissues. This obvious need did not escape the attention of previous investigators.

Kelly et al (Hermatoporphyrin derivative: possible aid in the diagnosis and therapy of carcinoma of the bladder. J Urol. 1976; 115:150-151); described the use of a hematoporphyrin derivative for detection and phototherapy of bladder cancer. Gill et al (1981, 1983, 1984, 1987; Selective surface staining of bladder tumors by intravesical methylene blue with enhanced endoscopic identification. Cancer. 1984; 53:2724-2727) demonstrated that certain dye substances gained entry into the abnormally permeable cancer cells and remained "fixed" in the cells' interiors. These same investigators showed that 92% of their subjects (patients) demonstrated selective staining of bladder tumors. But they did not evaluate how many of these cancers would have been detected by conventional viewing through a cystoscope without staining of tissues. Mufti et al (Diagnosis of clinically occult bladder cancer by in vivo staining with methylene blue. Br J Urol. 1990; 65:173-175) provided a more sober assessment when they noted that only half the stained sites that they biopsied revealed abnormalities in the urothelium. Almost all dye substances reported by Gill et al and Mufti et al are strongly ionised in the pH range 5-7 units, the most common range for bladder contents (urine). Mishina et al. (Absorption of anticancer drugs through bladder epithelium. Urology. 1986; 27:148-157), point out that passive permeation of solutes into the urothelium bears an inverse relationship to the degree of ionisation, the partition coefficient between lipids and water and molecular size. These same investigators also concluded that the penetration of methylene blue in rat bladders with cancer was similar in both cancerous and in normal urothelium.

Such approaches based on passive permeation of colored solutes did not find acceptance in every day urological practice because of some eminently practical reasons:

1. Damage of any sort to the bladder mucosa, be it previous radiotherapy/chemotherapy, infection, or even mechanical trauma caused by overfilling with the dye itself, all give rise to false positive stains.
2. Conversely, underfilling the bladder results in non uniform contact between the dye and bladder mucosa resulting in false negative areas of non-staining.
3. Meeting the conflicting requirements of staining (pre) cancerous mucosa and non staining of normal urothelium is rendered even more uncertain by the physiological function of the bladder itself.
4. The passive permeation revealed an overall low efficacy of penetration and staining of the bladder tissues.

Physiological Function of the Bladder

The bladder is a receptacle for bodily waste products and it functions so that this waste can be eliminated at times of choice. Intuitively it can be reasoned that the waste products are not reabsorbed to any significant extent during their residence time in the bladder, a fact that has been demonstrated by Hicks et al and other investigators. The physiological function of urothelium is such that significant absorption (or reabsorption) of even the smallest solutes is very limited. The concentration of a drug and/or a dye substance, its time of residence, lipophilicity, hydrophilicity, the degree of ionisation and the size of the particular molecule, all play roles. In fact, control of drug delivery into the bladder wall by the standard method, passive diffusion, is limited to varying the concentration of the agent, the volume instilled and the duration of contact with the bladder mucosa. The effect of the remaining variables is assumed from either clinical experience or educated guess work or both.

Essentially, control of delivery of dyes into the bladder wall for diagnostic or therapeutic purposes is very limited. It would be desireable to introduce an additional, controllable variable that dominates the effects of all those mentioned. The inventors found that by using an Electromotive Drug Delivery technology, this goal can be achieved.

Electromotive Drug Delivery

Electromotive Drug Delivery (EMDD) involves the transfer of solutes (drugs) into the body by an electromotive force. The term "electromotive delivery" comprises two distinct physical processes: Iontophoresis and Electrophoresis. Iontophoresis: Iontophoresis is the active of transport of ionic molecules into tissue by the passage of an electric current through a solution containing the molecules to be delivered, using an electrode of appropriate polarity, as described by Stillwell. (Electrical stimulation and iontophoresis. In: Krussen F. H., ed. Handbook of Physical Medicine and Rehabilitation. St. Louis Mo.: W. B. Saunders Company, 1971:2-Chap 14).

1. All drugs must be in ionized form and in aqueous solution (water, hydrogel).
2. Positively charged drug ions are repelled from the anode and negatively charged drug ions are repelled from the cathode, into underlying tissues.
3. Ionic transport of a solute in an electric field is described by the Nernst-Planck equation which states that: when a concentration gradient and electric field both exist, the ionic flux is the linear sum of the fluxes that would arise from each effect alone. (Planck, Keister et al: Planck M. uber die erregung von elektrizitat und warme in Elektrolyten Ann Phys Chem. 1890; 39:161-186. Keister J. C. et al. Ionic mass transport through a homogenous membrane in the presence of a uniform electric field. J Membrane Sci. 1986; 29:155-167).

$$Ji = -Di\frac{\Delta Ci}{\Delta x} + Di\frac{zeECi}{kT}$$

where Di is the diffusion coefficient, $\Delta Ci$ is the ionic concentration difference over a distance x, z is the valency and e the electron charge of the ion, E the electric field, k Boltzmann's constant and T is the absolute temperature.

4. Petelenz et al (U.S. Pat. No. 4,915,685) teach that electrical transport of a specific ion is proportional to the product of the concentration, the mobility, and the charge (valency) of the particular ion; and inversely proportional to the concentrations, mobilities and valencies of all other ions in solution.

Electrophoresis: Iontophoresis is associated with increased transport of water: as ions are driven into tissues by coulombic repulsion, each is accompanied by a hydration shell, a slight but significant movement of water which is termed electro-osmosis. In turn, this movement of water induces and enhances penetration of soluble, non electrolytes associated with the hydrations shells, a phenomenon that, for the purposes of this invention, is termed electrophoresis: solvent drag sums up the situation succintly. Measurements of its effect with the non-ionized drug, idoxuridine, and the negatively charged dexamethasone phosphate (which was transported into tissues against its coulombic gradient) were undertaken by Gangerosa et al. (Iontophoretic assistance of 5-iodo-2'-deoxyuridine penetration into neonatal mouse skin and effects on DNA synthesis. Proc Soc Exp Biol Ned. 1977; 154:439-443) and Glass et al. (The quantity and distribution of radiolabelled dexamethasone delivered to tissues by iontophoresis. International Journal of Dermatology. 1980; 19:519-525).

Early Studies by the Inventors

Realising the theoretical potential of electromotive drug delivery into the bladder for therapy of certain diseases, the inventors, Lugnani et al, (Iontophoresis of drugs in the bladder wall: equipment and preliminary studies. Submitted to Artificial Organs (AO). February 1992; Studio sperimentale sulla iontoforesi in vesciche di cadavere mediante sostanze coloranti. Accepted for publication in Proceedings Ital Urol Congress. June 1992); conducted an initial series of investigations in 10 cadaveric bladders. FIG. 2 demonstrates the experimental design in which two sealed cups, control (7) and experimental (8) each containing the same dye (9) were applied simultaneously; an active electrode (10) was inserted in the bladder and a dispersive electrode (11) was positioned to a convenient area of the external tissue. Electric current was applied to the experimental electrode (8) and no current was applied to the control cup (7). After 10 minutes the appropriate sections of bladder were washed with distilled water and examined by direct vision and then by light microscopy to assess the depth of dye penetration. The dyes used were methylene blue, gentian violet, doxorubicin (all positively charged) and indigo carmine (negatively charged). With all control tests there was some light, patchy staining of the outermost layers of epithelium. In sharp contrast, application of electric current resulted in deep, even penetration of all dyes tested through full thickness urothelium and often into the underlying lamina propria and muscularis tissues. Cadaveric tissue is always more permeable than its living counterpart and the inventors were reasonably certain that the differences in passive and electromotive dye delivery in living persons would have been even more distinctive. However, at the time of these experiments, Lugnani et al did not realize the potentialities offered by electromotive delivery of dyes for selectively localizing cancerous tissues, especially occult cancerous tissues.

Reliable simple techniques for localisation of occult bladder cancers are a high priority in the field of urology. This need is given emphasis in a recent editorial by Harris et al (Bladder cancer-field versus clonal origin. N Eng J Med. 1992; 326 (11): 759-761); who discuss the mounting evidence in favor of a monoclonal origin of bladder cancer and its subsequent early spread. Techniques aimed at exploiting abnormalities in cancer tissue by differential dye staining have been reported and results were decidedly mixed, with complete, partial and no success being reported. Perhaps the most reliable guide to these conflicting results is that the technique(s) has not been adopted in day-today urological practice although it has been available for more than 15 years.

Electromotive drug delivery is a century old art that is now emerging as a science. In essence, this technology provides accelerated, controllable drug delivery across biological membranes and into underlying tissues; particularly valuable attributes in transporting solutes into impermeable tissues such as the urothelium of the bladder.

SUMMARY OF THE INVENTION

It is a principal object of the invention to provide a novel method for localization of occult cancer of the bladder.

It is a further object of the invention to provide such a method which permits reliable and efficacious detection of said cancerous regions by visual inspection through an endoscope.

It is another object of the invention to provide such a method which, in addition to permitting detection of said cancerous regions, also provides therapy therefore.

It is yet a further object of the invention to provide a method as stated above also permitting an additional thermal coagulation therapy of cancerous sites.

It is also an object of the invention to enhance the reliability of a diagnostic and therapeutic method as stated above by providing means which enhance a selective localization of cancerous sites.

The above and other objects are achieved by a method for localisation of occult cancerous sites in the bladder, which comprises introducing into the bladder an electrically conductive aqueous solution comprising at least a physiologically acceptable dye substance, positioning in contact with said solution within the bladder a treatment electrode connected to a controllable source of electrical current, positioning outside the bladder on a convenient area of skin a dispersive electrode also connected to said controllable source of electric current, feeding electrical current to the electrodes whereby obtaining an electromotive delivery of said dye to the bladder tissues with a selectively greater absorption thereof in cancerous tissues and viewing the bladder by endoscopic means to locate cancerous sites.

In accordance with the process of the present invention, a water based solution containing ionized dye substances or non-ionized dye substances and ionized electrolytes is introduced into the bladder, a treatment electrode placed in a catheter is inserted into the bladder and a dispersive electrode is placed on the skin of the subject. A voltage differential is then applied to the treatment and dispersive electrodes with the polarity of the treatment electrode determined by the electrical charge of the instilled dye substances. As a result, dye substances are preferentially administered into cancerous regions. Visual identification of cancerous areas is further enhanced by increasing the elimination rate of dye substances from normal urothelium, which objective is achieved by heating the dye containing instillation fluid to 39° C.–43° C. or by intravesical instillation of the drugs having vasodilating effects such as lidocaine, mepivacaine, papaverine, guanethidine, verapamil, clonidine, prazosin, phenoxybenzamine, phentolamine.

According to a further embodiment by voltage control of the strength of the electrical field within the intravescical dye solutions, the current densities applied to cancerous areas for the administration of dyes are additionally increased whereby an electro-thermal coagulation of the localised cancerous sites is also achieved.

DETAILED DESCRIPTION OF THE INVENTION

CONCEPT

Figure 1:
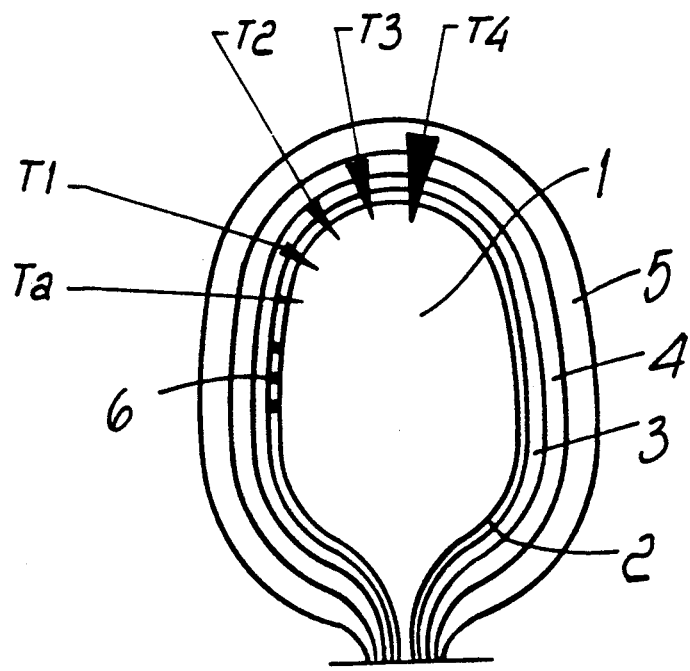
FIG. 1 is a view of a longitudinal section of a bladder showing schematically the known degree of penetration of tumors in the bladder wall.
Figure 2:
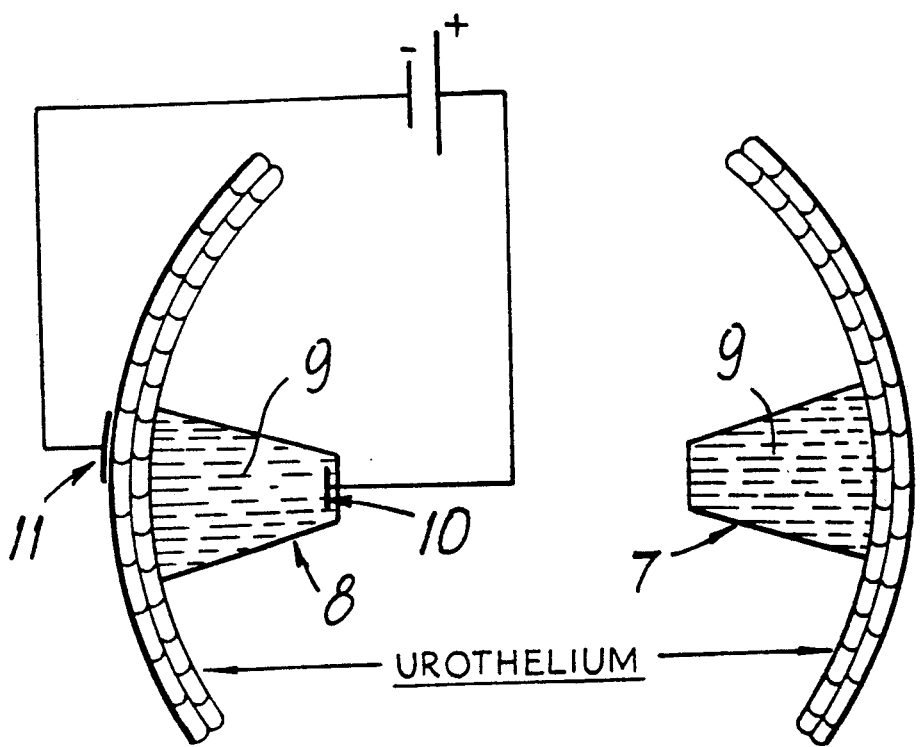
FIG. 2 is a schematic view of a prior art comparative experiment showing a bladder wall to which a dye is applied through an iontophoretic method in comparison with a control bladder wall to which a dye is applied through a non-electromotive delivery. In this experiment no cancerous areas and no selective dye delivery have been involved.

The genesis of this invention arose from the collation of five phenomena which are:
1. The inherent physiological limitations imposed upon earlier attempts to localize bladder cancers by-differential staining techniques using passive diffusion.
2. The discovery of the fact that the physical principles of EMDD, which imply preferential channeling of electric current into abnormal cancerous regions, enhance differential dye staining.
3. The exploitation of a normally undesirable side effect of EMDD: thermal damage to tissues (burning), in order to achieve thermal coagulation.
4. The exploitation of abnormalities in vessels supplying and draining blood to cancerous tissue further to accentuate the staining differential.
5. The realization that certain potent anti cancer drugs are colored substances that may be used both for localisation and treatment of bladder cancers.

RATIONALE

In accordance with the present invention, novel processes are disclosed for the localisation and treatment of occult cancers of the bladder which are characterized by the relatively large, but difficult to detect, flat endophytic lesions or by much smaller clumps of malignant and premalignant cells. Cancer of the bladder is a potentially lethal condition with cancer cells prone to seed throughout the bladder and eventually spread to other parts of the body. Random biopsies ("bladder mapping") are routinely employed to monitor the course of the disease but abnormal areas of tissue frequently remain undetected

EMDD

Pertinent to this invention are the electrical properties of the mammalian body, in which Suckling (Bioelectricity. MCGraw - Hill. New York, N.Y. 1961) depicted numerous electrical resistances both in series and in parallel. Watkins (A manual of electrotherapy 3rd edn. Lea and Febiger. Philadelphia, Pa., 1968), showed that electrical conductivity of various tissues correlates with their water content, so that the stratum corneum of the skin with only 20% water (the physiological average is 70%) offers the highest impedance while bodily fluids, such as blood and urine, have the lowest impedance. Soft tissues, composed of multitudes of cells, present a more complex situation. Singer et al (The fluid mosaic model of the structure of cell membranes. Science, 1972; 175:720); described the presently accepted model of the cell membrane which is composed of bilipid layers perforated at intervals by water channels of about 10 A° in diameter: intracellular channels. Similar intercellular water channels exist between cells and their diameter depends upon the type of tissue; between the closely packed urothelial cells, which form a virtual palisade lining the bladder cavity, the intercellular gaps are only about 15 A° in diameter, probably the narrowest of all tissues lining body cavities. All of these channels are of lower electrical resistance than the two lipid layers and will be subject to greater current density when electrical charge is applied.

Premalignant and malignant cells form tissues that are abnormal and which are served by a capricious blood supply. The majority of bladder cancers, both macroscopically and microscopically, are "friable" with abnormally wide microscopic channels and visually detectable gaps in some areas. Thus, bladder cancers offer less electrical resistance than does normal urothelium. Referring to the Nernst - Planck equation, when an electric field is applied to an ionized dye substance within the bladder cavity, the marginally distinctive passive component of ionic flux, $$-D_i \frac{\Delta C_i}{\Delta x},$$

will be greatly supplemented by the electrical component, $$D_i \frac{Z_e EC_i}{kt};$$

electrical current represented by ionic flux will funnel preferentially into the less resistive cancerous areas and differential dye staining between cancers and normal urothelium will be enhanced.

Nor do the advantages of EMDD end at this point. It is well known that inadvertent imposition of high current densities to small areas of skin lead to thermal tissue damage. (If the drug being applied is a local anesthetic agent, third degree burns may result, as one of the inventors can testify). Always regarded as the most undesirable (and expensive) complication of EMDD, this same complication becomes a therapy in accordance with the present invention: cancerous areas are submitted to higher current densities and may be thermally coagulated if the therapist so desires, which mimics standard effective treatment for cancer of the bladder (TUR). Also, voltage-controlled current sources are fast dissappearing because any tissue damage results in a drop in resistance which, in turn, brings about an increase in current strength (V=IR) and further tissue destruction. Again in accordance with this invention, this flaw in design becomes an attribute.

Vasodilatation

The well known therapeutic effect of heat upon cancers led the inventors to the concept of differential vasodilatation to aid in the selective localisation of bladder cancers. In the field of urology, the therapy is Mostly used for prostatic cancer employing expensive radiation machines. Servadio et al (Hyperthermia in the treatment of prostate cancer. The Prostate. 1981; 5:205-211), and the majority of investigators ascribe several reasons for the benefits of hyperthermia, with the most important one being: the pathological microcirculation of tumors prevents the—for normal tissues typical—heat distribution through vasodilatation. This results in a thermal load and subsequent tissue damage to the tumor.

Vasodilatation distributes more than heat. The basis of millions of injections given world wide every day is that the blood supply carries the drug away from its injection site to all, or most, bodily tissues: and the better the blood supply the faster the drug is relocated. An exactly analogous situation exists when dyes are instilled into a cancerous bladder whose blood supply to normal urothelium has been augmented by vasodilatation: dye is removed more rapidly from normal tissues than from cancerous tissues thereby accentuating the differential staining.

There are many ways to bring about localised vasodilatation. Application of electric current alone will do so; and not necessarily through a thermal mechanism. A wide variety of drugs also dilate normal blood vessels by many different mechanisms. Some, such as the narcotic agents heroin and morphine, obviously would not be used for this purpose but others with desireable effects are included in this invention and will be described subsequently.

PREFERRED EMBODIMENTS

EMDD Apparatus

Figure 3:
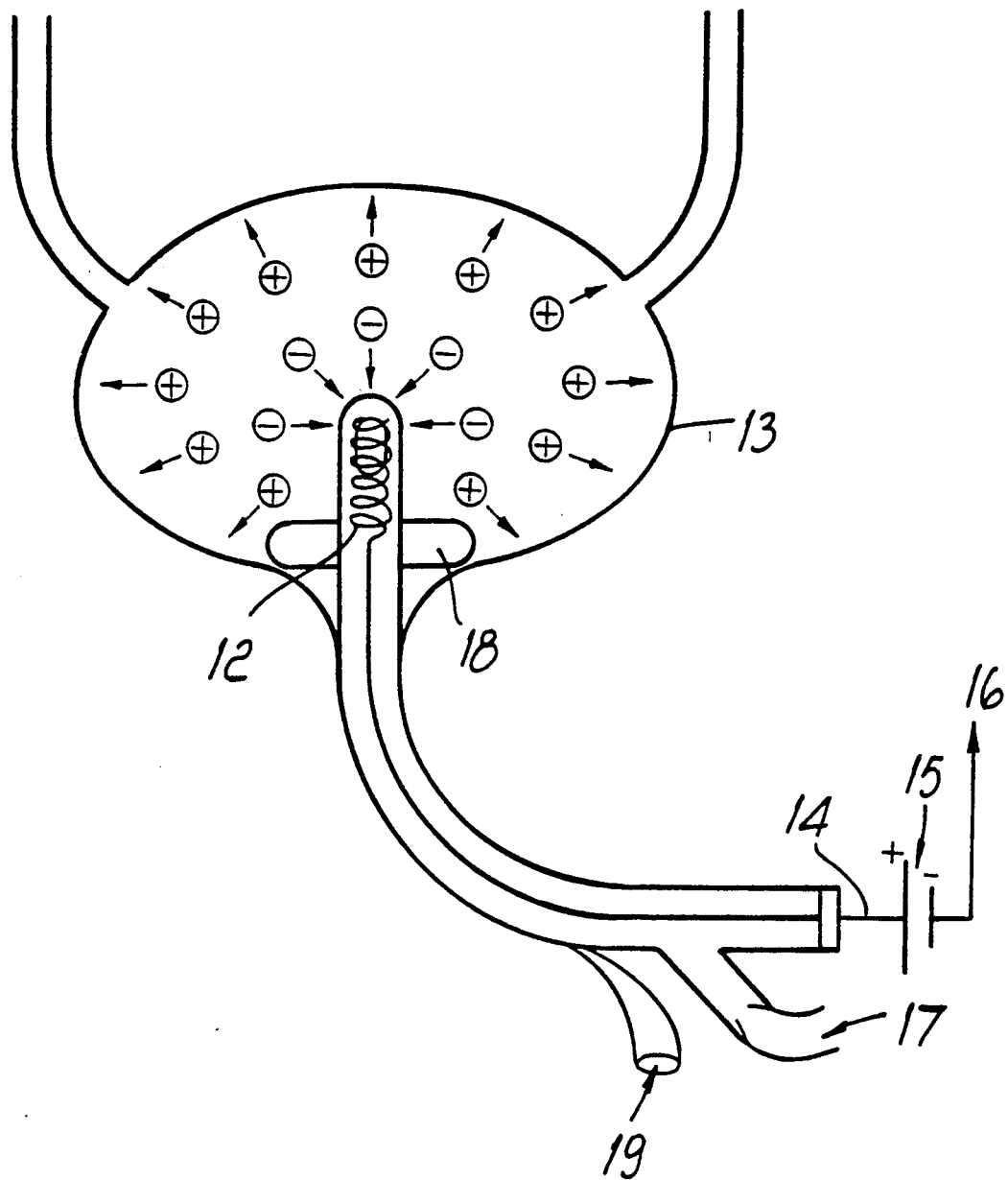
FIG. 3 is a schematic cross-sectional view of a bladder to which the method of localization of cancerous sites of the present invention is applied.

The inventors have considerable experience with electromotive administration of drugs and dyes within the bladder. Referring to FIG. 3, a catheter containing a spiral electrode (12) is inserted into the bladder (13), a balloon (18) fixed on the external wall of the catheter is by means of a conduit (19), inflated to delimit and to isolate the organ, either entirely or partially. The bladder is drained, "washed" with distilled water to remove residual urine and its ionic specie, and then the drug/dye solution (17) of volume 100 ml or more is infused. The conductive, insulated wire (14) leading to the electrode is connected to a voltage source (15) which is also connected to a dispersive electrode (16) (not shown) sited on some convenient area of skin and then a selected electric current is applied for a selected time intervals, depending upon the dyes/drugs used and the specific purpose of each individual procedure. The power source is equipped with both current control means and voltage control means of known type, and the power source is also equipped to deliver constant DC and pulsed DC.

As stated hereinbefore using voltage control means (such as transistors, filters, etc.) when delivering anticancer dye substances with the method of the present invention an additional electrocoagulation treatment can be achieved. In fact, since the current will preferentially travel to lower resistive cancer areas, some electrical damage to these areas will occur whereby resistance will drop further. With a voltage controlled machine, the current will rise causing more tissue damage - and so on, so that an electrocoagulation with an anticancer drug will also be performed in this way. When using voltage control means the voltage is generally maintained of from 20 to 60 volts.

Dye substances

There are numerous dye substances available for clinical and investigative use but those selected for this invention either are therapeutically inert, but have proven visual merits for diagnostic purposes, or are also therapeutically active having been applied intravesically as chemotherapeutic agents. Such dye substances which can be used for clinical or therapeutic purposes will be indicated herein as physiologically acceptable dyes.

Innocuous Dye Substances: The various blue dyes have visual merit and avoid the problems caused by red-green color blindness which, to some degree, afflicts about 1/20 of the male population, presumably including urologists. The dyes of this hue chosen by the inventors are methylene blue, toluidine blue and Evan's blue. Of other dyes tested by the inventors, gentian violet is selected. All of these dyes are supplied as positively charged ions in salt form. In the case of the use of these dyes for diagnostic purposes only, the EMDD treatment is carried out by applying preferably a current of 5-15 mA for 3-10 minutes. When the dye salts are used in solution by themselves, without addition of further electrolytes, their delivery to the bladder tissues occurs by iontophoresis.

Anticancer Dye Substances: Doxorubicin and its close chemical relative, epirubicin, are colored red which is not so visually striking in bladder tissue as the blue dyes but they are both effective anticancer drugs. Doxorubicin has undergone extensive testing in cadaveric bladders by the inventors and color changes are quite distinguishable. Mitomycin C (MMC) is probably the most effective chemotherapeutic agent available for localised treatment of bladder cancer, it is a violet color and has been investigated. Mitoxantrane is both a powerful blue dye and a potent anticancer drug and is under investigation at this time of writing. Doxorubicin, epirubicin and mitoxantrone are positively charged and are available as salts, e.g. the hydrochloride salts. When such salts are administered without addition to the solution of further electrolytes the delivery mechanism is by iontophoresis. In the pH range of 5-7 units, MMC is largely non-ionised whereby the presence of ionized electrolytes is critically required in the dye solution and its delivery mechanism is by electrophoresis, as explained above. When these anti cancer dye-drugs are administered for both diagnosis and therapeutic purposes, a preferred range of current applied is of 15 to 20 mA for 15-20 minutes, in order to obtain maximum differential dye staining benefits and therapeutic effect.

The concentrations proposed for all of the dye substances are low, extending from 0.01% to 0.1%, preferably from 0.04 to 0.1%. In this range the passive diffusive component is minimised, whereas the electrical component of transport will be largely unaffected: the absolute concentration of dye is reduced but so is that of its counterion and, as taught by Petelenz et al, all other ions in solution compete for charge with the drug ion to be administered. The low concentrations of chemotherapeutic dyes select themselves. Levels greater than 0.1% carry the risk of severe bladder inflammation and possible systemic toxicity.

The investigators have knowledge of prior art involving all of these dye substances. Methylene blue has been widely employed to test various physiological functions. It has been administered by iontophoresis to demonstrate sites of drug penetration through the skin and, as stated previously, has been used as a localising agent for occult bladder cancers by passive permeation and seemed not to be selective. To the inventors' knowledge, no other investigators have used EMDD with any dye substances for the purpose of localising occult bladder cancers.

Vasodilatation

It is a major objective of this invention to cause selective vasodilatation of vasculature supplying normal urothelium so as to enhance elimination of dye substances from this tissue and so accentuate the increased dye staining of cancerous regions. Of the numerous physical and chemical agents capable of achieving this aim, the following few are selected.

Heat: Heating the dye solutions instilled into the bladder is a simple, effective method of causing maximum vasodilatation of normal urothelial vasculature. The effect will be short lived, about 5-8 minutes depending upon the volume infused, because of the very effective heat exchange mechanism provided by normal, dilated vasculature. Applied in this manner, this modest degree of hyperthermia will most likely have no direct anticancer effect, although, as Hahn has described, it may enhance the actions of the anticancer dyes included in this invention. A preferred heating temperature is from 39° to 43° C.

Drugs: The drugs selected for their vasodilating effects have specific attribues pertinent to this invention: all are positively charged ions so that they match polarities with the selected dyes, MMC excepted; none cause localized tissue irritation or damage; and, given in correct dosage, have very few systemic side effects.

Lidocaine (HCl) and mepivacaine (HCl) are the most common agents used to provide local anesthesia for surgical procedures. A sometimes annoying (to the surgeon) side effect of these two drugs is continous oozing of blood caused by vasodilatation brought about by blockade of the sympathetic nerve supply to the operative field. When these drugs are instilled into the bladder in 0.5%–1.0% solutions and an electric current is applied, they provide effective local anesthesia (Lugnani et al) and marked vasodilatation of normal urothelial vasculature (unpublished data).

Papaverine (HCl) is a well known vasodilator which achieves its effects by direct action on the walls of blood vessels. When used in strengths of 0.5%–1% with said dye solutions, papaverine will produce maximum vasodilatation of normal urothelial blood vessels.

Guanethidine (sulphate) has a biphasic effect. This drug causes massive release of norepinephrine from sympathetic nerve terminals which causes an initial vasoconstriction lasting 3–5 minutes, then the released nor epinephrine is metabolised, the depleted nerve terminals can no longer release sufficient quantities of this hormone to maintain normal vascular tone and vasodilatation, lasting some hours, ensues. Guanethidine 10–100 mg. added to said dye solutions to give concentrations up to 0.1% will produce these effects.

Verapamil (HCl) is a calcium channel blocker and the only one that is available in ionised solution. All of these drugs have potent vasodilating properties and verapamil, 5–10 mg., added to said dye solutions to give concentrations up to 0.1% will produce the required vasodilatation.

Clonidine (HCl) is usually administered systemically as an antihypertensive agent but its modes of action include agonism of $\alpha_2$ adrenergic receptors which produces highly reproducible vasodilating effects when applied locally to normal blood vessels. Quantities of 0.1 mg–2.0 mg placed in said dye solutions to give concentrations of at most 0.1% will produce the desired vasodilatation.

Prazosin (HCl), phenoxybenzamine (HCl) and phentolamine (mesylate) are three $\alpha$ adrenergic blocking agents, which inhibit the vasoconstrictive actions of norepinephrine on its receptor sites. These agents are proven vasodilators and, when added individually and alone to said dye substances in quantities of 3 mg–10 mg to give concentrations equal to, or lower than 0.1% will produce the desired vasodilatation of normal urothelial blood vessels.

Matching Polarities

The dye substances, methylene blue, toluidine blue, Evans blue, gentian violet, doxorubicin, epirubicin and mitoxantrane are all supplied as positively charged ions and therefore their polarities match with those of all selected vasodilating drugs. The treatment electrode using the above agents and combinations thereof will be anodic and drug administration will be by iontophoresis in the absence of added electrolytes, or by combined iontophoresis and electrophoresis, when further electrolytes are added.

Mitomycin C, when administered as the sole drug or when used in conjunction with guanethidine or with verapamil or with clonidine or with prazosin or phenoxybenzatine or with phentolamine, will be mixed in physiological electrolyte solutions of osmolarities ranging 100 mosm–310 mosm, and an anodic treatment electrode is used. When MMC is used in conjunction with lidocaine or mepivacaine or papaverine solutions, an anodic treatment electrode is applied. In all of these applications MMC is administered by electrophoresis.

Addition of Electrolyte Solutions

In accordance with this invention, all dye substances and all drugs with vasodilating effect, with the exceptions of lidocaine, mepivacaine and papaverine, are prepared for administration in concentrations $\leq 0.1\%$ and these low concentrations are poor conductors of electric current. Advantageously this difficulty is overcome by the addition of physiological electrolyte solutions of osmolarities ranging from 100–310 mosm. In the sense of this invention, the term "physiological" does not necessarily imply matching solute osmotic pressures of body water and solutes (280–290 MOSM) but designates electrolytes commonly used in replacement therapies, $Na^+$ $K^+$ $Ca^{2+}$ $Cl^-$ $HCO_3^-$ $HPO_4^{2-}$ Lactate, in various combinations. The addition of electrolytes will increase charge competition for all drugs included in solution but they will diminish or counteract undesirable hydrolysis of water and will promote electrophoretic transport of said drugs, so that drug administration in the presence of electrolytes is achieved by combined iontophoresis and electrophoresis, except for the non-ionized MMC, which will be delivered as stated before, by electrophoresis.

EXAMPLES

Methylene Blue

In order to define minimum volumes required for uniform contact between the bladder wall and its infused dye contents, five patients scheduled for cystoscopy underwent intravesical infusion of methylene blue 0.1% and iontophoresis of the bladder contents using constant DC, 15 mA for 5–10 minutes. With 50 ml volumes there was a pronounced "leopard" effect with large areas of heavy staining, light staining and no staining. With intravesical volumes of 100 ml or more, there was deep, even staining of all visible areas of the bladder wall.

Based on this and further investigation it was found that a preferable amount of dye solutions to be used according to the invention is from 100 to 400 ml.

Mitomycin C

Seven patients scheduled for total cystectomy were subjects for preoperative and intraoperative, intravesical insitilldtion of MMC. Three patients, control subjects, received instillations of MMC, 40 mg in 50 ml water about one hour before operation, the bladders were drained intraoperatively of 100–150 ml (MMC+urine) over times of 60–90 minutes after instillation. Four patients, experimental subjects, were infused with MMC, 40 mg in 100 ml 0.9% saline, which was electrophoresed into the bladder wall using an anodic electrode and pulsed DC, 15 mA for 15 minutes, then the bladders were drained of their 110-130 ml contents.

Immediately after the bladders were removed they were sectioned and examined visually. The three bladders from control subjects showed light, patchy violet staining of the urothelium with no obvious differences between cancerous and normal tissues. The four bladders from the experimental subjects demonstrated obviously increased, violet staining of normal urothelium as compared to that in control subjects, and an equally obvious, deep purple staining of numerous cancerous areas.

Lidocaine and Mepivacaine

The inventors have personally supervised more than 200 instillations of lidocaine (HC1) or mepivacaine (HC1) into the bladder and their subsequent iontophoretic administration (15-20 mA for 15-20 minutes) to obtain local anesthesia for TUR of cancers. The protocol calls for the simultaneous intravesical administration of the powerful vasoconstrictor, epinephrine, which enhances both the effectiveness and the duration of local anesthesia.

Fortuitously, epinephrine was omitted in a recent treatment and a color differential became obvious on direct viewing through the endoscope and on the viewing screen. The scarlet hue of normal urothelium was visibly enhanced because of vasodilatation whereas areas of cancerous tissue showed no change in color and appeared as slightly paler patches scattered throughout normal urothelium: there was no vasodilatation in the cancerous regions. Thus, the above result shows the utility in EMDD of vasodilating agents in enhancing the visualization of cancerous sites.

As it can be seen from the foregoing, the present invention provides an efficaceous and reliable method for localising cancerous sites in bladder which is based on the discovery that the electromotive delivery of dyes improves remarkably the selective absorption thereof by the cancerous tissues.

It is to be understood that the preliminary, abovedescribed examples are only illustrative of the application of the present invention. Numerous modifications and alternatives may be devised by those skilled in the art without departing from the spirit and scope of the present invention and the appended claims are intended to cover such modifications and arrangements.

We claim:

1. A method for localisation of occult cancerous sites of tissues of a bladder, which comprises introducing into the bladder an electrically conductive aqueous solution comprising at least a physiologically acceptable dye substance, positioning in contact with said solution within the bladder a treatment electrode connected to a controllable electrical current source, positioning outside the bladder on a convenient area of skin a dispersive electrode also connected to said controllable electric current source, feeding an electrical current to the electrodes to obtain an electromotive delivery of said dye substance to the bladder tissues with a selectively greater absorption thereof in cancerous tissues, and viewing the bladder by endoscopic means to locate greater dye absorption areas.

2. A method according to claim 1, wherein said dye substance is selected from the group consisting of methylene blue, toluidine blue, Evans blue and gentian violet, each in the form of an ionizable salt thereof.

3. A method according to claim 2, wherein said dye substance is contained in said solution at a concentration ranging from about 0.01% to about 0.1%.

4. A method according to claim 2, wherein said electrical current has an intensity of about 5-15 mA and is applied for about 3-10 minutes.

5. A method according to claim 1, wherein said dye substance is selected from anticancer dye drugs, whereby both a localisation and treatment of cancerous sites of the bladder is achieved.

6. A method according to claim 5, wherein said anticancer drug is selected from: doxorubicin, epirubicin, mitoxantrane and mitomycin C.

7. A method according to claim 6, wherein said anticancer dye drug is doxorubicin, epirubicin or mitoxantrane, each in an ionizable salt form.

8. A method according to claim 6, wherein said anticancer dye drug is mitomycin C in a non-ionizable form mixed and wherein said anticancer dye drug is mixed in an electrolyte solution of an osmolarity in the range of about 100 to 310 mosM.

9. A method according to claims 7 or 8 wherein said electrical current has an intensity of about 15-20 mA and is applied for about 15-20 minutes.

10. A method according to claim 5, wherein said anticancer dye drug is used in said solution at a concentration ranging from about 0.04% to about 0.1%.

11. A method according to claim 5 wherein the voltage of the electrical current source is maintained in a range of from about 20 to about 60 volts during the electromotive drug delivery, thereby further achieving an electrocoagulation of said cancerous sites.

12. A method according to claim 1, wherein a volume of about 100 to 400 ml of said dye solution is introduced into the bladder.

13. A method according to claim 1, wherein said solution of said dye substance is preliminarily heated to a temperature in the range of about 39 C.-43 C.

14. A method according to claim 1, wherein said dye solution also comprises an agent having a vasodilating effect.

15. A method according to claim 14, wherein said agent with a vasoldilating effect is selected from a group consisting of papaverine, guanethidine, verapamil, clonidine, prazosin, phenoxybenzamine, phentolamine, their physiologically acceptable salts and their mixtures.

16. A method according to claim 14 wherein said agent with vasoldilating effect is selected from lidocaine and mepivacaine.

17. A method according to claim 1, wherein said aqueous solution further comprises physiologically acceptable electrolytes having osmolarities ranging from about 100 to about 310 mosM.

18. A method according to claim 17, wherein said electrolytes are selected from a group consisting of $Na^+$, $K^+$, $Ca^{2+}$, $Cl^-$, $HCO_3^-$, $HPO_4^{2-}$, lactate and their mixtures.

* * * * *